United States Patent

Heyde

[11] Patent Number: 4,991,428
[45] Date of Patent: Feb. 12, 1991

[54] ION CHROMATOGRAPHY METHOD FOR LOW CONCENTRATIONS

[76] Inventor: H. Paul Heyde, 206 Loma Bonita Dr., San Luis Obispo, Calif. 93401

[21] Appl. No.: 412,112

[22] Filed: Sep. 25, 1989

[51] Int. Cl.[5] .............................................. G01N 30/08
[52] U.S. Cl. .................................... 73/61.1 C; 422/70
[58] Field of Search ...................... 73/61.1 C; 422/70; 436/161; 210/198.2, 656

[56] References Cited

U.S. PATENT DOCUMENTS

| | | | |
|---|---|---|---|
| 3,559,458 | 2/1971 | Hrdina | 73/61.1 C X |
| 3,975,946 | 8/1976 | Ball et al. | 73/61.1 C |
| 4,102,782 | 7/1978 | Saito et al. | 73/61.1 C X |
| 4,699,718 | 10/1987 | Jones et al. | 73/61.1 C X |
| 4,715,216 | 12/1987 | Müller | 73/61.1 C |

Primary Examiner—Hezron E. Williams
Assistant Examiner—Joseph W. Roskos
Attorney, Agent, or Firm—Daniel C. McKown

[57] ABSTRACT

A technique for measuring concentration of ions in the parts per trillion range ($10^{-5}$ to $10^{-6}$ milligram per liter) uses a new interconnection of ordinary components in a four step technique. In the first two steps, standard solutions of known, but widely different, concentrations are measured to determine a calibration factor (C) which is then applied in the second two steps to determine the very weak unknown concentration of the sample. The process can be automated and is useful in applications such as nuclear power plants where the presence of even very small concentrations of certain ions is undesirable because of the extreme conditions prevailing.

1 Claim, 5 Drawing Sheets

ION CHROMATOGRAPHY METHOD FOR LOW CONCENTRATIONS

BACKGROUND OF THE INVENTION

1. Field of the Invention

The present invention is in the field of ion chromatography and specifically relates to a technique for measuring concentration of ions in the parts per trillion range ($10^{-5}$ to $10^{-6}$ milligram per liter).

2. The Prior Art

The cost of shutting down a large power plant for repairs or maintenance may be as much as $140,000 per hour. Clearly, it is in the interest of the owner to take such measures as may be available to increase the length of time between such occurrences.

Corrosion of the pipes in a steam-generating installation is a major concern. Corrosion weakens the pipes and could lead to a dangerous situation if not controlled. The high pressures and temperatures used in contemporary steam plants greatly accelerates the corrosion process and thereby shortens the life of the installation.

In an effort to reduce corrosion, power plant operators have continually attempted to improve the purity of the water used. The presences of certain ions in the water is especially undesirable, and a substantial effort is made to reduce the concentration of those ions.

In order to reduce the concentration of harmful ions in the water, it is necessary to be able to measure their concentration with satisfactory accuracy. Typically, the concentration of those ions is in the range $10^{-4}$ to $10^{-6}$ mg/l. Considerable difficulty is encountered in measuring such minute concentrations. The instrument most commonly used is an ion chromatograph. As normally used, a prepared sample of accurately known concentration and volume is conducted through the chromatograph, and it produces a reading that is measured. Thereafter, a sample of unknown concentration is also run through the chromatograph, and the magnitude of its reading is compared to the magnitude of the reading produced by the sample of known concentration. The liniarity of the instrument being well-known, the concentrations are in proportion to the readings produced.

This procedure is quite acceptable so long as a sample of known concentration, also called the standard sample, is available. However, it is very difficult to obtain and maintain samples in the parts per trillion range. At such extraordinarily low concentrations, the sample readily becomes contaminated, not only from the vessels that contain it, but also from any air that may come in contact with the sample. In practice, concentrations on the order of parts per billion ($10^{-3}$ mg/l) represent the practical limit for field use and for use in automatic measuring equipment.

In addition to the possibilities of contamination, it is not practical to obtain a parts per trillion standard merely by mixing a small amount of parts per billion standard with a large quantity of water. The water itself is not sufficiently pure.

This lack of a practical concentration standard in the parts per trillion range has impeded efforts to measure concentrations in that range by use of the ion chromatograph.

At these concentrations, there was little prior art to guide the present inventor, who has devised his own solution to the problem.

The method used by the present inventor is believed to be novel, notwithstanding the fact that some elements of the apparatus used by the present inventor are known in the art.

For example, in U.S. Pat. No. 3,559,458 issued Feb. 2, 1971, Hrdina states that it is known to insert a sample from a capillary tube into a buffer stream by the use of manually-operated valves. He also states that the use of a special multiway valve to connect a loop containing a sample to a gas stream circuit is known in gaseous chromatography.

In U.S. Pat. No. 3,975,946 issued August 24, 1976, Ball, et al. describe a sample introduction apparatus that includes a valve body that has at least one fluid passage of precisely defined volume, which receives and holds the sample. Thereafter, the valve body is rotated to permit a carrier liquid to positively displace the precisely defined volume of sample fluid into the chromatograph.

In U.S. Pat. No. 4,102,782, issued July 25, 1978 Saito, et al. teach the use of a pulse motor to drive a syringe for the purpose of accurate sample introduction.

U.S. Pat. No. 4,715,216 issued Dec. 29, 1987 to Muller describes apparatus and method for the determination of low ion concentrations in aqueous specimens by ion chromatography at the parts per billion level. This patent typifies the state-of-the-art at the time of the present invention.

SUMMARY OF THE INVENTION

The object of the present invention is to permit determination of the concentration of a particular ion in a liquid at concentration levels on the order of, typically, one-thousandth the concentration of the same ion in a standard solution. Thus, if the concentration in the least concentrated standard available is 10 parts per billion ($10^{-2}$ mg/l), the present invention will permit measuring concentration in the 10 parts per trillion ($10^{-5}$ mg/l) range.

In accordance with a preferred embodiment of the present invention, apparatus is set up to permit liquid to be conducted from either a first source or from a second source through a concentrator column, a separator column, and a conductivity cell. The time-integrated conductivity is measured for each source. The same volume $V_S$ is always drawn from a first source, and the same volume $V_L$ is always drawn from the second source, where $V_L$ is several orders of magnitude less than $V_S$.

Once this apparatus, which will be described in detail below, has been set up, the following experimental procedure is followed. From the first source, a sample of volume $V_S$ and accurately known concentration $K_{S1}$ is supplied to the conductivity cell by way of the concentrator column and the separator column, and the conductivity reading A is noted. Next, a sample of nominal volume $V_L$ and accurately known concentration $K_{L1}$ is drawn from the second source, and the conductivity reading B produced by it is noted.

Next, a sample of nominal volume $V_L$ and accurately known concentration $K_{L2}$ is run through the system, and the conductivity reading D is noted. The known concentration $K_{L2}$ is the least concentrated standard available. Thereafter, a sample of volume $V_S$ and unknown concentration $K_{S2}$ is run, and the conductivity reading E is noted. The unknown concentration $K_{S2}$ is in a range several orders of magnitude less than the concentration $K_{L2}$. Finally, the unknown concentration $K_{S2}$ is determined from the relationship $$\frac{E}{D} = \frac{A}{B} \frac{K_{L1}}{K_{S1}} \frac{K_{S2}}{K_{L2}}$$

The novel features which are believed to be characteristic of the invention, both as to organization and method of operation, together with further objects and advantages thereof, will be better understood from the following description considered in connection with the accompanying drawings in which a preferred embodiment of the invention is illustrated by way of example. It is to be expressly understood, however, that the drawings are for the purpose of illustration and description only and are not intended as a definition of the limits of the invention.

DETAILED DESCRIPTION OF THE PREFERRED EMBODIMENT

In a conventional procedure for using an ion chromatograph, a sample of a standard concentration $K_{S1}$ and volume $V_S$ is run through the chromatograph and the integrated conductivity reading A is noted. Then, a specimen of unknown concentration $K_{S2}$ and volume $V_S$ is run through the instrument and its integrated conductivity reading B is noted. The reading A is proportional to the volume $V_S$ and to the concentration $K_{S1}$, i.e., $$A = e_1 V_S K_{S1} \quad (1)$$

Likewise, $$B = e_2 V_S K_2 \quad (2)$$

The quantities $e_1$ and $e_2$ may be considered to be constants of proportionality, or alternatively, they may be thought of as efficiencies with which the ions present are converted to integrated conductivity readings by the instrument.

The assumption is universally made that $e_1 = e_2$, permitting the unknown concentration to be found by the relationship $$\frac{K_{S2}}{K_{S1}} = \frac{B}{A} \quad (3)$$

In typical usage, the readout device of the chromatograph is calibrated by the operator so that the reading A equals full scale or 100% or, for example, 100 parts per billion. The reading B is then expressed as some percentage of full scale and is read directly from the scale in parts per billion.

In connection with equation (3), several noteworthy points are usually unappreciated. It is not necessary to know the volume $V_S$, so long as it is the same for the standard and for the specimen. Also, there is an implicit assumption that the efficiency of the instrument is independent of the concentrations. This assumption is true over a couple of orders of magnitude in concentration for a typical instrument.

However, if the concentration of the specimen is less than, say, one percent of the concentration of the standard, it becomes difficult to measure the integrated conductivity of the specimen with adequate accuracy.

The problem faced by the present inventor was even more difficult. The concentration of the least concentrated standard conveniently available was 10 parts per billion ($10^{-2}$ mg/l), but the concentration of the specimen to be measured was on the order of 10 parts per trillion ($10^{-5}$ mg/l). Conventional techniques were not applicable.

His solution to the problem was to find a way to compare a small sample of nominal volume $V_L$ of the least concentrated standard available against a much larger nominal volume $V_S$ of the specimen to be measured. The word "nominal" is used because neither volume is known precisely or measured precisely in using the technique of the present invention. It is only essential that from one measurement to the next $V_L$ should be the same and that $V_S$ should be the same.

Figure 1:
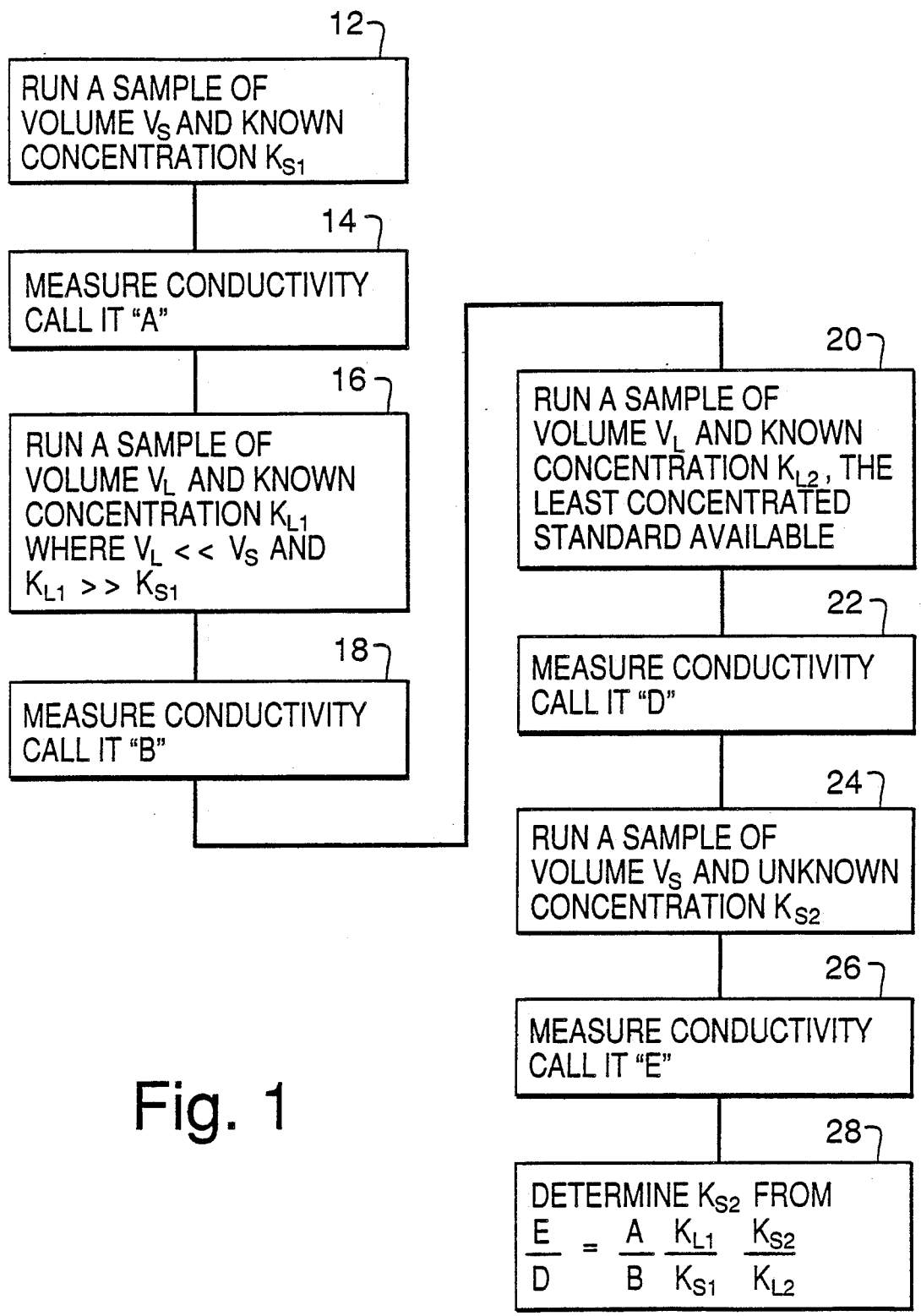
FIG. 1 is a flow chart showing the steps in a preferred embodiment of the method of the present invention.

In accordance with a preferred embodiment of the present invention, as shown at blocks 12 and 14 of the flow chart of FIG. 1, a sample of accurately known concentration $K_{SI}$ and nominal volume $V_S$ is run through the instrument and an integrated conductivity reading A is obtained. In a typical working example $V_S$ is approximately 20 ml and $K_{SI}$ is 100 parts per billion ($10^{-1}$ mg/l)

The reading A is represented as $$A = e_{VS} V_S e_{KS1} K_{SI} \quad (4)$$

where $e_{VS}$ is a factor reflecting the deviation of the actual volume of the sample processed from its nominal value $V_S$ and $e_{KS1}$ is an efficiency factor for the concentration level used.

Next, in accordance with the preferred embodiment, as shown at blocks 16 and 18 of the flow chart of FIG. 1, a sample of accurately known concentration $K_{L1}$ and nominal volume $V_L$ is run through the instrument and an integrated concentration reading B is obtained. In the working example, $V_L$ is approximately 20 $\mu$l and $K_{L1}$ is 100 parts per million (100 mg/l).

The reading B may be represented as $$B = e_{VL} V_L e_{KL1} K_{L1} \quad (5)$$

where $e_{VL}$ is a factor reflecting the deviation of the actual volume of the sample processed from its nominal value $V_L$ and $e_{KL1}$ is an efficiency factor for the concentration used.

In the next step, represented by blocks 20 and 22 of the flow chart of FIG. 1, a sample of nominal volume $V_L$ and of the least concentrated standard available is run through the instrument. Its concentration $K_{L2}$ in the working example is 10 parts per billion ($10^{-2}$ mg/l), and again $V_L$ is approximately 20 μl. The resulting reading D may be represented as $$D = e_{VL} V_L e_{KL2} K_{L2} \tag{2}$$

where $e_{VL}$ is the same as before and $e_{KL2}$ is an efficiency factor applicable at the concentration level used.

The procedure to this point may be thought of as having calibrated the instrument, which is now ready to measure the unknown concentration of a specimen in the parts per trillion range.

In the next step, represented by blocks 24 and 26 of the flow chart of FIG. 1, a sample of the specimen of unknown concentration $K_{S2}$ and volume $V_S$ (the same volume as in the step of block 12) is run through the instrument. The resulting reading E may be represented as $$E = e_{VS} V_S e_{KS2} K_{S2} \tag{7}$$

where $e_{VS}$ is the same factor as in the step of block 12, and $e_{KS2}$ is an efficiency factor applicable at the concentration level used. In the working example, $V_S$ is nominally 20 ml, From equation (4) above, $$e_{VS} V_S = \frac{A}{e_{KS1} K_{S1}} \tag{8}$$

and from equation (5)

$$e_{VL} V_L = \frac{B}{e_{KL1} K_{L1}} \tag{9}$$

Substituting the expressions of equations (8) and (9) into equations (7) and (6), respectively, yields:

$$E = A \frac{e_{KS2} K_{S2}}{e_{KS1} K_{S1}} \tag{10}$$

and $$D = B \frac{e_{KL2} K_{L2}}{e_{KL1} K_{L1}} \tag{11}$$

From (10) and (11), $$\frac{E}{D} = \frac{A}{B} \frac{e_{KL1}}{e_{KS1}} \frac{e_{KS2}}{e_{KL2}} \frac{K_{L1}}{K_{S1}} \frac{K_{S2}}{K_{L2}} \tag{12}$$

If it were not for the presence of the fractions $$\frac{e_{KL1}}{e_{KS1}} \text{ and } \frac{e_{KS2}}{e_{KL2}}$$

one could solve for the desired ratio $$\frac{K_{S2}}{K_{L2}},$$

since the remaining quantities are known.

By experimentation the present inventor has confirmed his insight that $$\frac{e_{KS1}}{e_{KL1}} = \frac{e_{KS2}}{e_{KL2}}. \tag{13}$$

This implies that the fractional loss of efficiency per order of magnitude change in concentration is approximately independent of the absolute value of the concentration. It is also consistent with a different hypothesis, namely, that all of the efficiencies are the same. Whatever the correct theory may be, the present inventor has found that the desired ratio $$\frac{K_{S2}}{K_{L2}}$$

can be found from the equation $$\frac{E}{D} = \frac{A}{B} \frac{K_{L1}}{K_{S1}} \frac{K_{S2}}{K_{L2}} \tag{14}$$

as shown at block 28 of the flow chart of FIG. 1. This equation may be rewritten as $$\frac{K_{S2}}{K_{L1}} = C \frac{E}{D} \tag{15}$$

where the quantities $K_{S2}$, $K_{L2}$, E and D are the variables of the last two steps (blocks 20, 22, 24 and 26), and where C is a correction factor obtained from the first two steps (blocks 12, 14, 16 and 18), where $$C = \frac{B}{A} \frac{K_{S1}}{K_{L1}} \tag{16}$$

Referring back to equations (4) and (5) it can be seen that $$C = \frac{e_{VL} V_L e_{KL1}}{e_{VS} V_S e_{KS1}} \tag{17}$$

Now it is seen that equation (15) has the same form as equation (3) except for the correction factor C. This shows that the conventional procedure discussed at the beginning of this section can be used, but because of the different sizes of the nominal volumes $V_S$ and $V_L$, a simulated dilution of $$\frac{V_L}{V_S}$$

has been obtained by use of the four-step technique of the present invention.

One not familiar with the problems of working at these extremely low concentration might imagine that the various samples are poured from a beaker into a funnel-like receptor on the chromatograph, and similar over-simplifications. Such is definitely not the case.

Practically everything the sample comes in contact with has a tendency to contaminate the sample to an extent that would render the measurements useless. In practice, elaborate precautions are taken to prevent contamination. In particular, the entire process is sometimes carried out in a closed system to prevent contamination from the air, and any open containers are blanketed with a layer of an inert gas, such as argon.

Hence it was, that after conceiving of the technique of simulated dilution, the present inventor had to devise apparatus to implement the technique, subject to all of the constraints imposed by the extraordinary weakness of the concentrations.

Naturally, the present inventor made full use of existing components, much as an electronic engineer would use resistors, capacitors and transformers to make a new circuit. In this sense, the fluid circuit that implements the technique of the present invention is believed to be a new combination and interconnection of the existing components. That fluid circuit is shown at various stages of the method in FIGS. 2-5.

Figure 2:
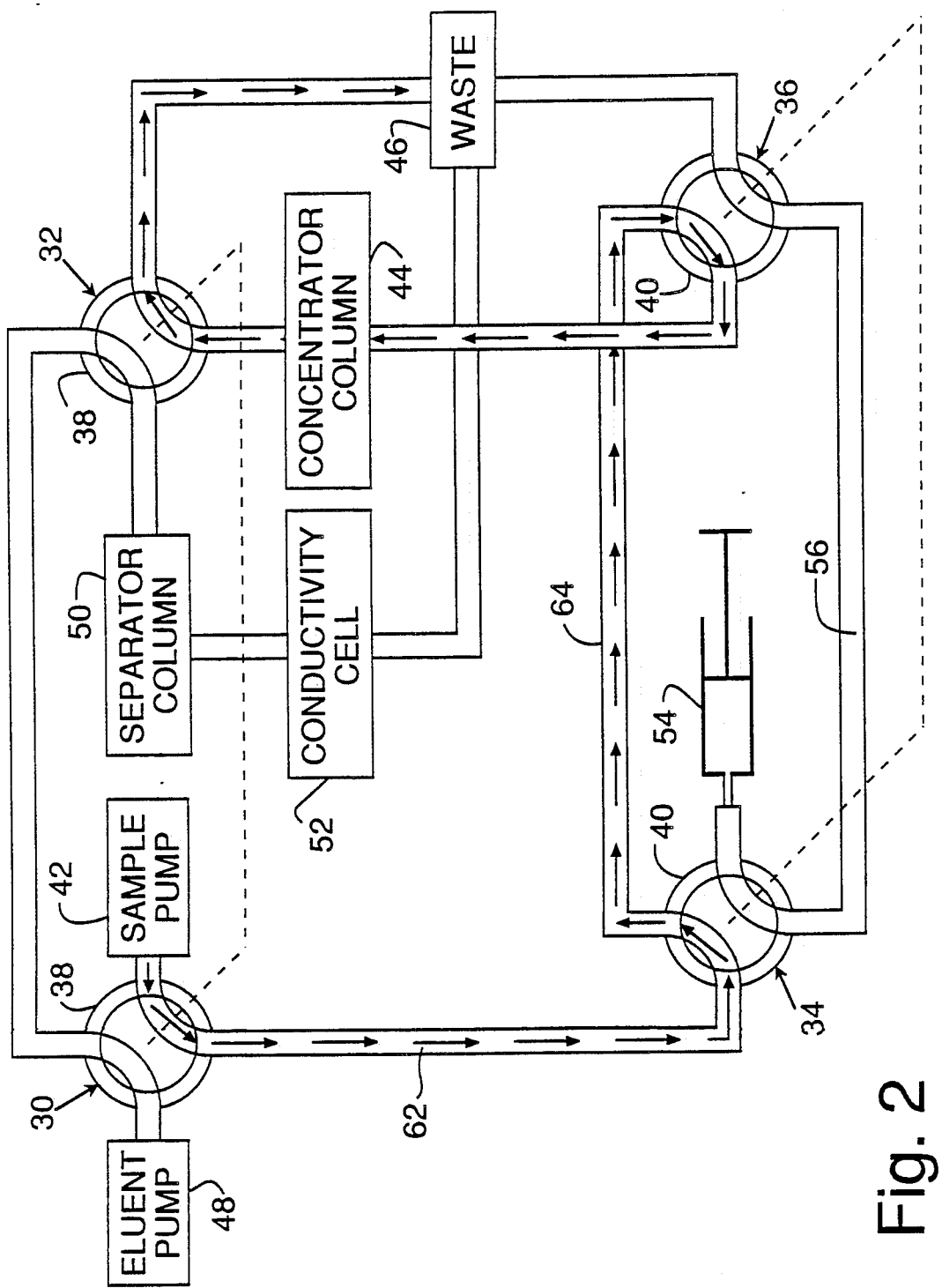
FIG. 2 is a diagram showing the configuration of the apparatus of a preferred embodiment when a sample of volume $V_S$ is being loaded into the concentrator.

As shown in FIG. 2, the fluid circuit includes two double-gang valves 30, 32 and 34, 36. The valves 30 and 32 are connected by a common shaft (actually the common rotatable core of the valves) so that their positions relative to the common fixed body 38 of the valve can be altered simultaneously by the operator to direct the flow of liquid through the valve, as indicated by the dashed line connecting the valves 30 and 32.

Likewise, the valves 34 and 36 operate in unison under control of the operator, so that their positions relative to the common fixed body 40 can be altered simultaneously. The valves 30, 32 are independent of the valves 34, 36.

The components shown and the plumbing that interconnects them remain the same throughout FIGS. 2-5; however, in carrying out the steps of the method described above, the operator manipulates the valves 30, 32, 34 and 36 to alter the flow paths of the liquids. Reference will be made to the specific components in the course of the discussion below.

FIG. 2 shows the flow paths during the step of the method shown in block 12 of FIG. 1. With the valves 30, 32 and 34, 36 in the positions shown, a sample pump 42 loads a volume $V_{S1}$ of a standard having known concentration $K_{S1}$ through the conduits 62 and 64 and into concentrator column 44. To provide a flow path from the sample pump through the concentration column 44, the sample liquid must be routed by the valve 32 to a waste receptacle 46. In the working example, $V_S$ is 20 ml and $K_{S1}$ is 100 parts per billion ($10^{-1}$ mg/l).

Figure 3:
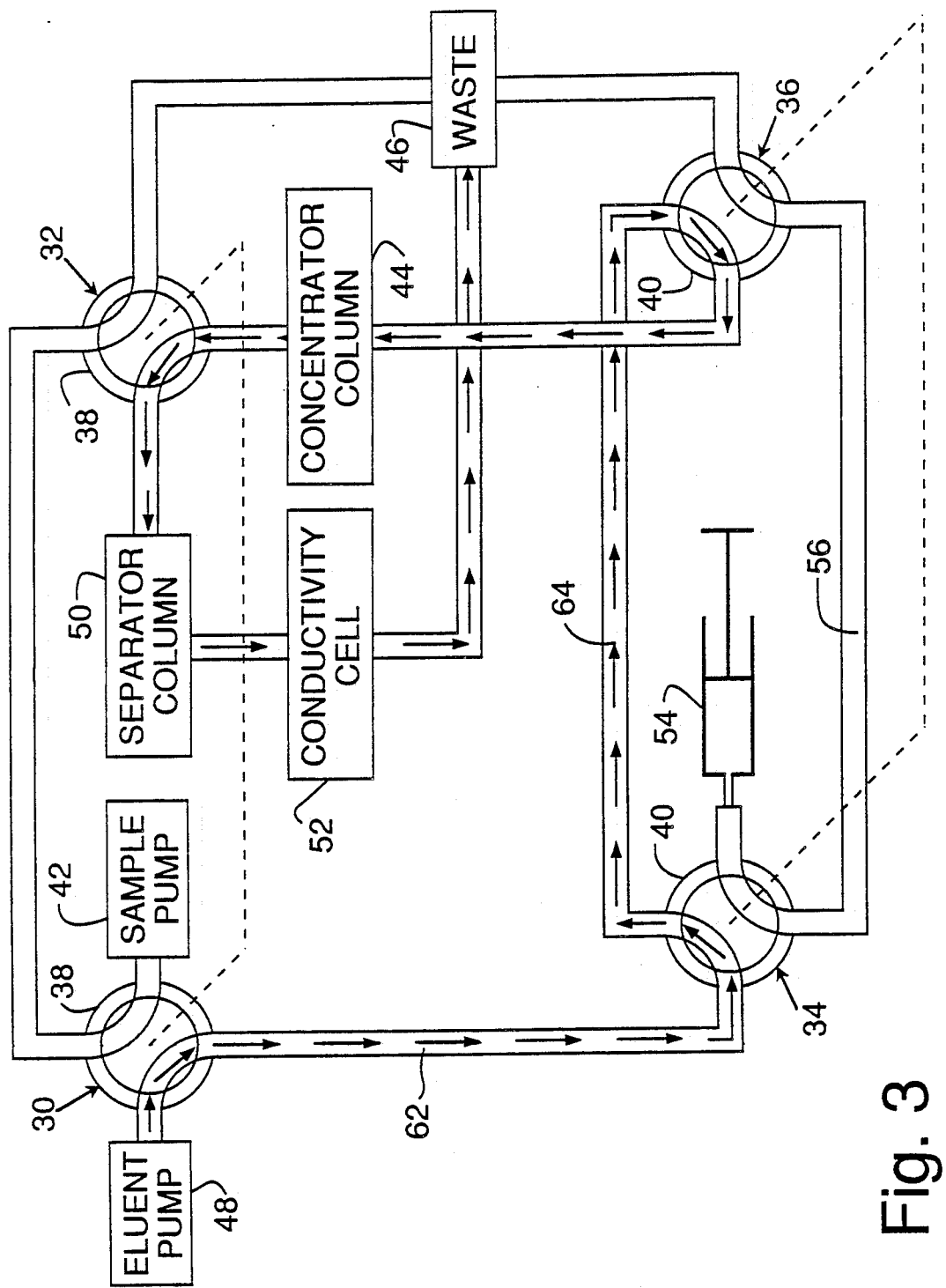
FIG. 3 is a diagram showing the configuration of the apparatus of a preferred embodiment when the conductivity of the sample of FIG. 2 is being measured.

After the concentrator column 44 has been loaded with the sample, the operator repositions the valves 30, 32 to the positions shown in FIG. 3, to permit an eluent pump 48 to pump eluent into the concentrator column 44 to drive the ions through the valve 32, through a separator column 50, and then through a conductivity cell 52, from which the liquid is discharged into the waste receptacle 46. The conductivity cell 52 produces an integrated conductivity reading A, of block 14 of FIG. 1.

Figure 4:
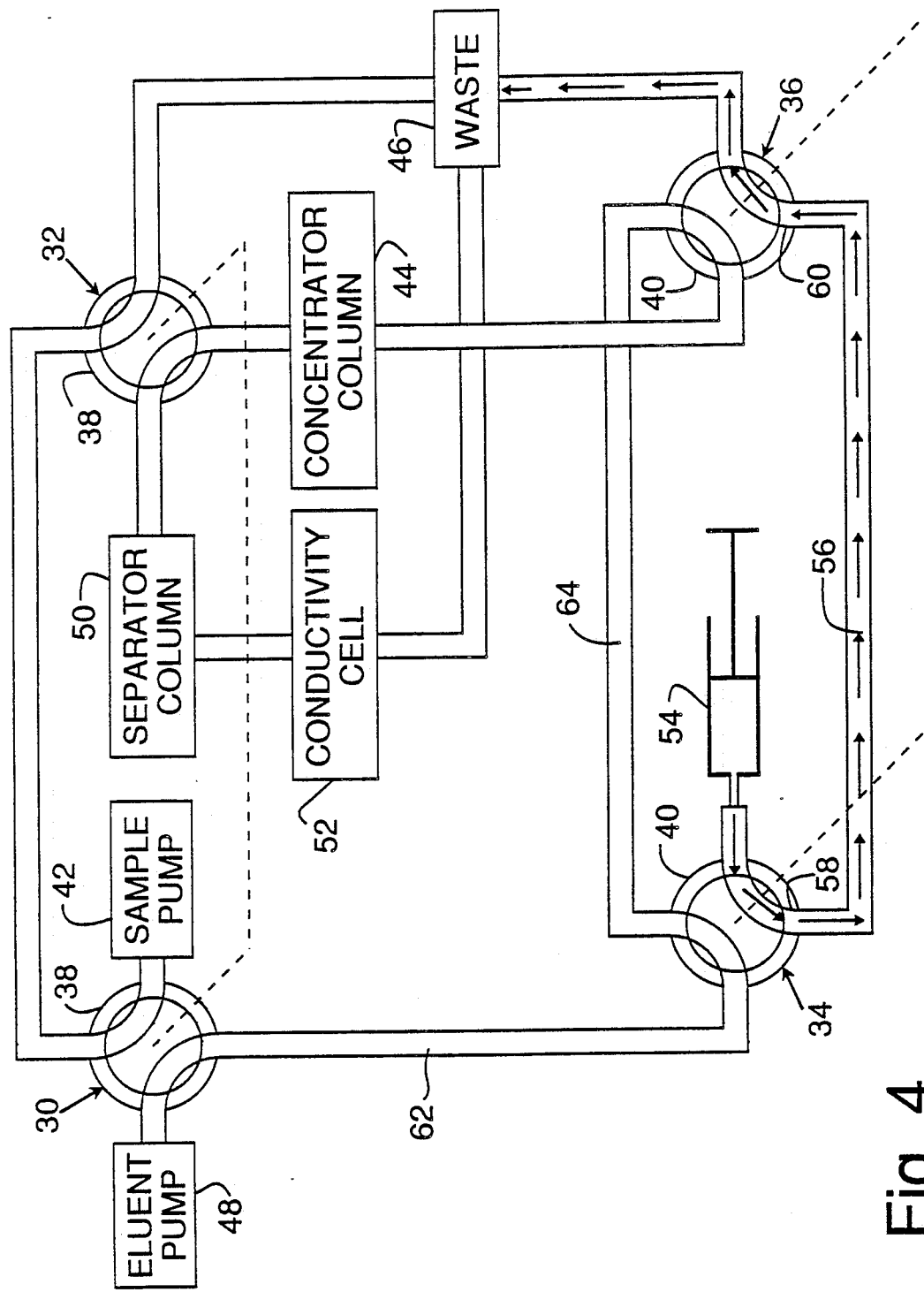
FIG. 4 is a diagram showing the configuration of the apparatus of a preferred embodiment when a small fixed volume $V_L$ of a standard sample is being measured; and, FIG. 5 is a diagram showing the configuration of the apparatus of a preferred embodiment when the conductivity of the sample of FIG. 4 is being measured.

Next, the operator sets the valves 30, 32, 34 and 36 to the positions shown in FIG. 4, and uses the syringe 54 to inject a relatively small quantity $V_{L1}$ of a standard of known concentration into the loop 56. The loop 56 consists of a short length of approximately 0.5 mm I.D. tubing that connects a port 58 on the valve 34 to a port 60 on the valve 36. The internal volume $V_{L1}$ of the loop in the working example is 20 l, and the concentration $K_{L1}$ is 100 parts per million (100 mg/l). The conduit 62 remains filled with eluent from the step of FIG. 3. The volume $V_{L1}$ includes the volume of the conduits within the cores of the valves 34 and 36.

Figure 5:
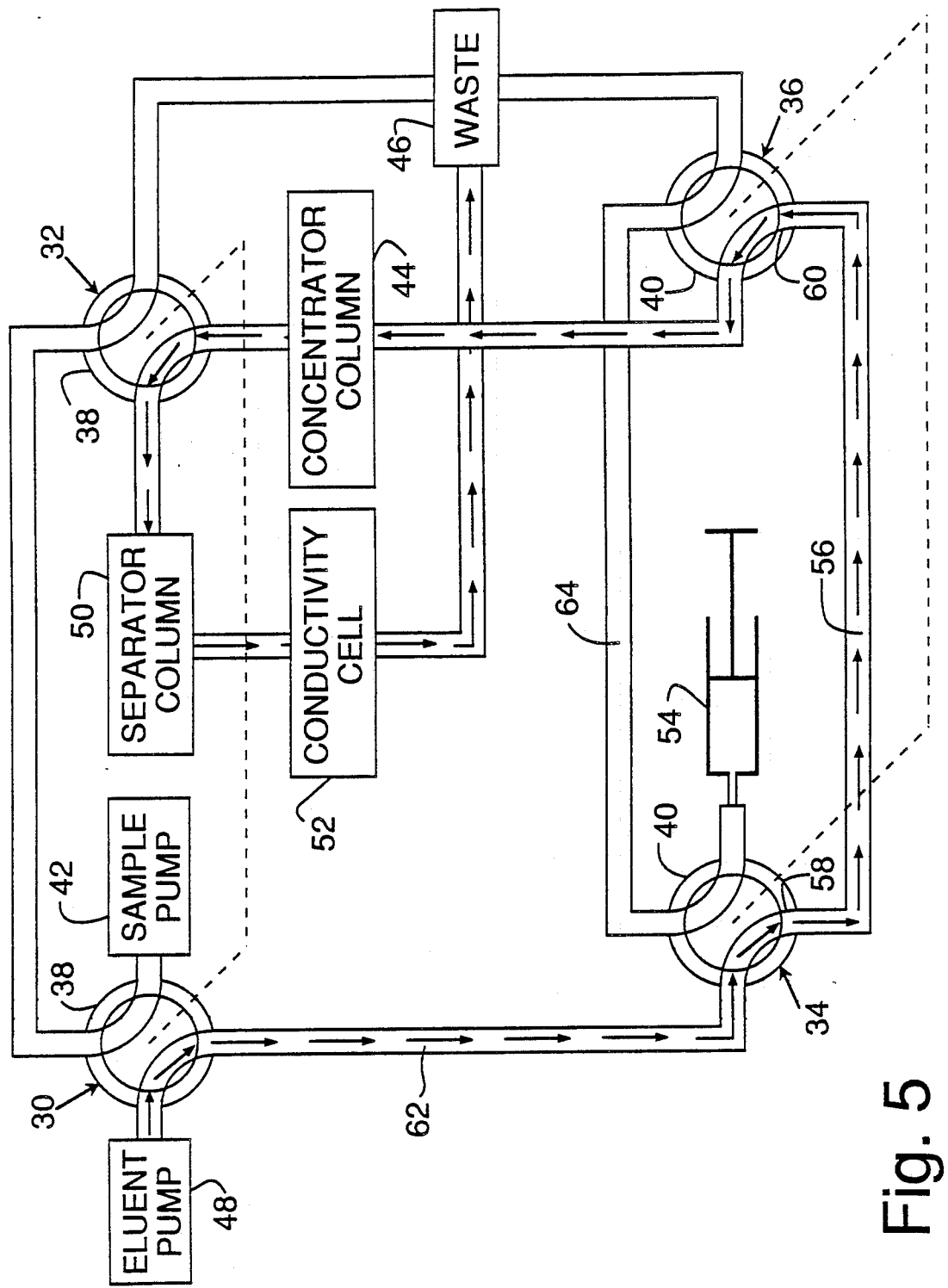

Next, the operator sets the valves 30, 32, 34 and 36 to the positions shown in FIG. 5 and the eluent pump 48 is used to pump the sample of volume $V_{L1}$ from the loop 56, through the concentrator column 44, the separator column 50 and the conductivity cell 52. The latter produces an integrated conductivity reading B, referred to at block 18 of FIG. 1.

Thereafter, the apparatus is rinsed by flushing with deionized water while cycling the valves. This step is essential because of the wide range of concentrations used.

Next, the operator sets the valves 30, 32, 34 and 36 to the positions shown in FIG. 4, and a quantity $V_{L2}$ is injected into the loop 56 by means of the syringe 54. So far as possible, $V_{L2} = V_{L1} = V_L$, but in this second injection the least concentrated standard available is used; its concentration is denoted by $K_{L2}$.

Thereafter, the valves 30, 32, 34 and 36 are set to the positions shown in FIG. 5 and the eluent pump 48 is used to drive the injected liquid through the concentrator column 44, the separator column 50 and the conductivity cell 52 as shown in FIG. 5. The integrated conductivity reading obtained is denoted as D, as shown in block 22 of FIG. 1.

At this point the apparatus has been calibrated and is ready for introduction of the sample of unknown concentration. The operator sets the valves 30, 32, 34 and 36 to the positions shown in FIG. 2 and a quantity $V_{S2}$ of the liquid of unknown concentration is loaded into the concentrator column 44 by the sample pump 42. So far as possible $V_{S2} = V_{S1} = V_S$, and in the working example $V_{S2}$ equals 20 ml. The unknown concentration is denoted by $K_{S2}$.

Next, the operator sets the valves 30, 32, 34 and 36 to the positions shown in FIG. 3 and the eluent pump 48 is used to drive the sample through the separator column 50 and the conductivity cell 52 as shown in FIG. 3. The resulting integrated conductivity is denoted by E as shown in block 26 of FIG. 1.

Finally, the operator uses the known quantities A, B, D, E, $K_{S1}$, $K_{L1}$, and $K_{L2}$ to calculate the unknown concentration $K_{S2}$ by use of the equation $$\frac{E}{D} = \frac{A}{B} \frac{K_{L1}}{K_{S1}} \frac{K_{S2}}{K_{L2}}.$$

As in any measurement, the precision of the measurement can be improved by repeatedly sampling the measured quantity, at least to the extent that the errors are random. That is true for the method of the present invention, but with an added refinement. As discussed above in connection with equation (15), the first two runs corresponding to blocks 12, 14, 16 and 18 of FIG. 1 are made to determine a correction factor C, which is applied to the ratio of E to D derived from the subsequent two runs corresponding to blocks 20, 22, 24 and 26 of FIG. 1. Accordingly, the number of repetitions of the first two runs may be chosen to be different from the chosen number of repetitions of the second two runs. In particular, the present inventor has found it desirable to repeat the first two steps using a second set of two known standard concentrations $K'_{S1}$ and $K'_{L1}$ to verify the value of the correction factor C.

Such variations on the method and apparatus as would be apparent to workers in the field of ion chromatography are considered to be within the scope and spirit of the present invention. For example, it should be understood that the four runs that together make up the method could theoretically be done in any order; although, the order described is preferred because it simplifies the practical aspects of calibrating the instrument. Likewise, it should be understood that the valves 30, 32, 34 and 36 can be replaced by a number of individual valves, each of simpler construction. Finally, the entire process can easily be carried out autonomously using electrically-operated valves whose successive positions are programmed in accordance with the flow chart of FIG. 1.

In conclusion, there has been described a method and apparatus for measuring ionic concentrations in the parts per trillion range. The apparatus is readily assembled from the components normally found in a chromatography lab, and the method can readily be learned and practiced by a skilled technician.

What is claimed is:

1. Apparatus for use in an ion chromatographic method for measuring ionic concentrations in the parts per trillion range, comprising in combination:

a sample pump (42);

an eluent pump (48);

a first conduit (62) having an input end and an output end;

first valve means of selectively connecting the input end of said first conduit to said sample pump and for selectively connecting the input end of said first conduit to said eluent pump;

a syringe (54);

a loop conduit (56) having an input end and an output end;

a second conduit (64) having an input end and an output end;

second valve means for selectively connecting the output end of said first conduit to the input end of said second conduit, for selectively connecting the output end of said first conduit to the input end of said loop conduit, and for selectively connecting said syringe to the input end of said loop conduit;

a concentrator (44) having an input port and an output port;

a waste receptacle (46)

third valve means for selectively connecting the output end of said second conduit to the input port of said concentrator, for selectively connecting the output end of said loop conduit to the input port of said concentrator, and for selectively connecting the output end of said loop conduit to said waste receptacle;

a separator (50) having an input port;

fourth valve means for selectively connecting the output port of said concentrator to said waste receptacle, and for selectively connecting the output port of said concentrator to the input port of said separator.

* * * * *